United States Patent [19]

Kondoh et al.

[11] Patent Number: 5,603,937
[45] Date of Patent: Feb. 18, 1997

[54] **IMMUNE-ENHANCING FOOD COMPRISING ISARIA TYPE INSECT RAISED FUNGUS (*CORDYCEPS JAPONENSIS*) AS A MAIN INGREDIENT**

[75] Inventors: Yoshikazu Kondoh, 8-19, Tsunogoro 1-chome, Aoba-ku, Sendai-shi, Miyagi 980; Nobuo Yahagi, 374-1, Oazakamabuchi, Mamurokawa-machi, Mogami-gun, Yamagata 999-53, both of Japan

[73] Assignees: Yoshikazu Kondoh; Nobuo Yahagi; Kabushiki Kaisha Ajiyoshi, all of Kyoto, Japan

[21] Appl. No.: 390,960

[22] Filed: Feb. 21, 1995

[30] Foreign Application Priority Data

Feb. 23, 1994 [JP] Japan .................................. 6-025280

[51] Int. Cl.⁶ .......................... A61K 35/78; A01N 63/00
[52] U.S. Cl. .................. 424/195.1; 424/93.5; 435/254.1; 514/885
[58] Field of Search .............................. 424/195.1, 93.5; 435/254; 514/885

Primary Examiner—John W. Rollins
Attorney, Agent, or Firm—Seed and Berry LLP

[57] ABSTRACT

An immune-enhancing food comprising a fruit body (sexual generation and nonsexual generation), a mycelium and a metabolite fluid of an Isaria-type insect-raised fungus (*Cordyceps Japonensis*) as a main ingredient of the food.

7 Claims, 2 Drawing Sheets

IMMUNE-ENHANCING FOOD COMPRISING ISARIA TYPE INSECT RAISED FUNGUS (*CORDYCEPS JAPONENSIS*) AS A MAIN INGREDIENT

CROSS-REFERENCE TO RELATED APPLICATION

This application claims priority from Japanese Application Serial No. 6-25280, filed Feb. 23, 1994.

TECHNICAL FIELD

The field of the present invention is immune-enhancing foods, particularly those comprising a fruit body (sexual generation and nonsexual generation), a mycelium and a metabolite fluid of an Isaria-type insect-raised fungus (*Cordyceps Japonensis*) as a main ingredient of the food.

BACKGROUND OF THE INVENTION

The immune reaction is known to be involved in the development of many diseases such as inflammation, tumor, allergy, autoimmune disorders, implantation rejection reaction (graff versus host disease) and the like. However, reduced immune reaction may cause higher susceptibility to infections with various viruses, bacteria and fungus, and can also cause increased incidence of a tumor.

The term "immune-activating agent" was used originally to mean the agents that enhance anti-tumor immunity. Then, the term came to be used to mean the agents that provide recovery from reduced or deteriorated immune system functions caused by foreign factors such as drugs or irradiation, as well as other factors such as acquired immunodeficiency syndrome and malignant tumors. Currently, immune-activating agents are not only used for immuno-therapy of a tumor, but are also used independently or in combination with a recombinant vaccine for the purpose of enhancing non-specific resistance in a host against various infections.

Some immune-activating agents are made from materials that have traditionally been used as folk remedies for the purpose of enhancing non-specific resistance, such as Basidiomycota including Kofukisaruno koshikake fungus (*Elfvingia applanata*), Meshimakobu-fungus and Shiitake fungus (*Lentlinus edodes*) as well as Otane ninjin fungus and Eleutherococ. Such fungi are taken orally and are referred to as Japanese and Chinese folk medicines. However, these folk medicines should, instead, be called "immune-enhancing foods" when their effects are viewed immunologically. An immunological study in experimental animals revealed that Basidiomycota organisms exhibited an immunological function-activating effect [1),2)] only when administered intraperitoneally or intravenously as extracts or independent ingredients, and that Otaneninjin did not provide such effects.[3)] Oral administration of these materials provided no immunological function-activating effect.

[1)] Chihara, *Pharmacia Review* 6:119 (1981) and references
[2)] Akiyama and Hamuro, *Proteins, Nucleic Acids and Enzymes* 26:208 (1981) and references cited therein
[3)] Hayashi et al., *Journal of Kanazawa Medical University*, 3:171(1978)

Japanese TOKKYO KOKAI No. 54-80486 discloses a method of artificial incubation of a nonsexual fungus of the family *Cordyceps Japonensis* and a method of preparing an extract or a powder of an active ingredient from the incubated mycelium. Japanese TOKKYO KOKOKU No. 61-53033, invented by one of the inventors and applicants of the present invention, N. Yahagi, discloses a method of artificial incubation of *Cordyceps Japonensis*, and describes some nourishing and vitalizing effects, and some anti-cancer effects, of *Cordyceps Japonensis*.

However, the immune-enhancing foods discussed above, derived from traditional, naturally occurring drugs, have not objectively shown effects in any immunological study in animal experiments. For the purpose of using an immune-enhancing food in a self-controlled therapy in these days, an immune-enhancing food having objectively proven activity is desired.

SUMMARY OF THE INVENTION

An object of the present invention is to provide an immune-enhancing food comprising a fruit body (sexual generation and nonsexual generation), a mycelium and a metabolite fluid of Isaria-type insect-raised fungus (*Cordyceps Japonensis*) as a main ingredient, which food has been proven to be immunologically active in animal experiments, and which food can be objectively proven to be active.

Another object of the present invention is to provide a food having improved immune-enhancing effects by means of admixing certain materials with the fruit body (sexual generation and nonsexual generation), a mycelium and a metabolite fluid of Isaria-type insect-raised fungus (*Cordyceps Japonensis*) described above.

DETAILED DESCRIPTION OF THE INVENTION

In studying the artificial incubation of Isaria-type insect-raised fungus (*Cordyceps Japonensis*), we, the present inventors, found surprisingly that the fruit body (sexual generation and nonsexual generation), the mycelium and the metabolite fluid of an Isaria-type insect-raised fungus (Cordyceps Japonensis), such as Hanasanagitake-fungus (*Isaria japonica* Lloyd) and Konasanagitake-fungus, enhance the immune system according to an immune activation test. Then, after much further effort, we established a method of using an artificial medium (Japanese TOKKYO KOKOKU No. 61-53033 etc.) to obtain the bulk of a mycelium that shows morphological characteristics similar to those of naturally-occurring insect-raised fungi. After inoculating the mycelium to a liquid medium, we obtained the fruit body (sexual generation and nonsexual generation), the mycelium and the metabolite fluid of the insect-raised fungus.

In addition, by admixing Ogi-fungus extract, beta-carotene, polypore extract and other fruit body with the fruit body (sexual generation and nonsexual generation), the mycelium and the metabolite fluid of this insect-raised fungus, we achieved further enhancement of immune-activating effect.

With regard to the amounts of the materials to be admixed with the fruit body (sexual generation and nonsexual generation), the mycelium and the metabolite fluid as mentioned above, when represented hereinafter by parts by weight, it is preferable that 0.1 to 2 parts by weight of Ogi-fungus extract, 0.1 to 1 part by weight of beta-carotene and 1 to 10 parts by weight of polypore extract are added to 100 parts by weight of the fruit body (sexual generation and nonsexual generation), the mycelium and the metabolite fluid.

Isaria-type insect-raised fungi (*Cordyceps Japonensis* organisms) that may be employed in the present invention are listed below.

| Fruit Body layers No. | Name | No. | |
|---|---|---|---|
| 1 | C. Nutans Pat. | 36 | C. crinalis Ellis |
| 2 | C. tricentri Yasuda | 37 | C. konnoana K.S. |
| 3 | C. takaomontana Ya. Ku | 38 | C. sobolifera (Fill.) Ber. et Br. |
| 4 | C. sphecocephala (K. 1) Sacc. | 39 | Cordyceps sp. |
| 5 | Torrubiella sp. | 40 | Isaria atypicola Yasuda |
| 6 | P. citrina K. S | 41 | Isaria sp. |
| 7 | C. militaris (Vuill) Fr. | 42 | C. purpureostromata K. S |
| 8 | Torrubiella sp. | 43 | Cordyceps sp. |
| 9 | C. nakazawai Kawamura | 44 | Paecilomyces sp. |
| 10 | C. ophioglossoides Fr. | 45 | Cordyceps sp. |
| 11 | Isaria japonica Yasuda | 46 | Isaria sp. |
| 12 | Gibellula aranearum II. Sy | 47 | C. cuboidea K. S |
| 13 | Torrubiella sp. | 48 | C. stylophora Ber. et Br. |
| 14 | C. unilateralis Sacc. | 49 | C. prolifica Kobayashi |
| 15 | C. ochraceostromata K. S | 50 | C. cochlidiicola K. S |
| 16 | C. martialis Speg | 51 | C. pruinosa Pet. |
| 17 | C. agriota Kawamura | 52 | Cordyceps sp. |
| 18 | Isaria farinosa Fr. | 53 | Cordyceps sp. |
| 19 | Hirsutella nutans | 54 | Paecilomyces sp. |
| 20 | C. albida K. S | 55 | C. chichibuensis K. S |
| 21 | Tilachlidiopsis nigra Ya et Ku | 56 | Paecilomyces sp. |
| 22 | Isaria sp. | 57 | C. japonensis Hara |
| 23 | C. facis K. S | 58 | Hirsutella sp. |
| 24 | C. termitophila K. S | 59 | Cordyceps sp. |
| 25 | C. dipterigena Ber. | 60 | Isaria sp. |
| 26 | Gibellula sp. | 61 | Torrubiella sp. |
| 27 | C. pseudolongissima K. S | 62 | Podonectrioides cicadellidicola K. S |
| 28 | C. elateridicora K. S | 63 | C. aurantia K. S |
| 29 | T. neofusiformis K. S | 64 | Cordyceps sp. |
| 30 | C. macularis f. sp | 65 | Hirsutella sp. |
| 31 | T. ryukyuensis K. S | 66 | Cordyceps sp. |
| 32 | Isaria sp. | 67 | Isaria sp. |
| 33 | C. oxycephala Penz et Sacc. | 68 | Torrubiella sp. |
| 34 | C. cochlidiicola K. S | 69 | Shimizuomyces paradoxa Kobayashi |
| 35 | Cordyceps sp. | 70 | Torrubiella sp. |
| 71 | C. ferruginosa K. S | 106 | C. geniculata f. sp. K. S |
| 72 | C. ferruginosa K. S | 107 | Cordyceps sp. |
| 73 | Hirsutella sp. | 108 | Cordyceps sp. |
| 74 | Podonectrioides citrina | 109 | C. alboperitheciata |
| 75 | C. coccidiicola K. S | 110 | C. michiganensis Mains |

-continued

| Fruit Body layers No. | Name | No. | |
|---|---|---|---|
| 76 | C. heteropoda K. | 111 | C. paradoxa K. |
| 77 | C. tuberculosum (Leb.) Mair. | 112 | C. obliquiordinata K. S |
| 78 | Cordyceps sp. | 113 | C. roseostromata K. S |
| 79 | Hymenostilbe odonatae K. | 114 | C. inegoensis K. |
| 80 | C. sinclairii K. | 115 | C. kusanagiensis K. S |
| 81 | Torrubiella sp. | 116 | C. militaris f. sphaerocephala (Schw) Fr. |
| 82 | Hirsutella coccidiicola | 117 | C. Clavata K. S |
| 83 | C. rubrostromata K. | 118 | C. hiugaensis K. S |
| 84 | Cordyceps sp. | 119 | C. falcatoides K. S |
| 85 | Isaria takamizusanensis K | 120 | C. geniculata K. S |
| 86 | C. rubiginosoperitheciata | 121 | C. crinalis Ellis ex Lloyd |
| 87 | Cordyceps sp. | 122 | C. entomorrhiza Link |
| 88 | Torrubiella sp. | 123 | C. ramosostipitata K. S |
| 89 | Cordyceps sp. | 124 | C. intermedia Imai |
| 90 | C. macularis Mains | 125 | C. jezoensis Imai |
| 91 | C. pseudoatrovirens K. | 126 | C. valvatostipitata K. S |
| 92 | C. tuberculata (leb.) Mair. | 127 | C. japonica Lloyd |
| 93 | C. tuberculata moelleri | 128 | C. ophioglossoides (Ehr.) Fr. |
| 94 | C. ootakiensis K. S | 129 | C. delicatostipitata K. S |
| 95 | C. subsessilis Petch | 130 | C. canadensis Ell. et Everh. |
| 96 | C. elongatostromata K. S | 131 | C. minazukiensis K. S |
| 97 | C. myrmecogena K. S | 132 | C. michinokuensis K. S f. intermedia |
| 98 | C. imagamiana K. S | 133 | Cordyceps sp. |
| 99 | C. gracilioides sp. | 134 | Torrubiella ellipsoidea K. S |
| 100 | C. neovolkiana K. | 135 | Torrubiella neofusiformis K. S |
| 101 | Cordyceps sp. | 136 | Torrubiella rosea K. S |
| 102 | Cordyceps sp. | 137 | Torrubiella globosa K. S |
| 103 | Cordyceps sp. | 138 | Torrubiella globoso-stipitala K. S |
| 104 | C. coccidioperitheciata | 139 | Torritbiella leioptis (Mains) K. S |
| 105 | Cordyceps sp. | 140 | C. nelziniboides K. S |
| 141 | C. pseudonelumboides | 176 | Torrubiella sp. |
| 142 | T. aurantia K. S | 177 | Cordyceps sp. |
| 143 | T. flava Petch | 178 | C. pallidiolivacea K. S |
| 144 | T. lonngissima K. S | 179 | C. pleuricapitats K. S |
| 145 | T. minutissima K. S | 180 | C. nigripoda K. S |
| 146 | T. aranicida Boud. | 181 | C. unilateralis Sacc. var. clavata (Kob.) K |
| 147 | Torrubiella sp. | 182 | C. carabidiicola K. S |
| 148 | C. yahagiana K. S | 183 | C. elongatoperitheciata K. S |
| 149 | Cordyceps sp. | 184 | C. kanzashiana K. S |
| 150 | T. superficialis K. S | 185 | C. ogurasanensis K. S |
| 151 | C. discoideocapitata K. S | 186 | C. minutissima K. S |
| 152 | C. longissima K. | 187 | C. osuzumontana K. S |
| 153 | Cordyceps sp. | 188 | C. polycephala K. S |
| 154 | C. ramosopulvinata K. S | 189 | C. prolifica f. terminalis K. |
| 155 | C. nipponica K. | 190 | C. superficialis f. crustacea K. S |
| 156 | C. myrmecogena K. S | 191 | C. superficialis (Peck.) Sacc. |
| 157 | Isaria sp. | 192 | C. uchiyamae K. S |
| 158 | Cordyceps sp. | 193 | C. scarabaeicola K. |
| 159 | Torrubiella sp. | 194 | C. staphylinidaecola K. S |
| 160 | T. minuta K. S | 195 | C. nigrella K. S |
| 161 | T. miyagiana K. S | 196 | C. hepialidicola K. S |

-continued

| Fruit Body layers No. | Name | No. | |
|---|---|---|---|
| 162 | Torrubiella sp. | 197 | *C. ovoideoperitheciata* K. S |
| 163 | Synnematium sp. | 198 | *C. alba* K. S |
| 164 | *C. pleuricapitata* f. sp. | 199 | *C. iriomoteana* K. S |
| 165 | Cordyceps sp. | 200 | *C. ogurasanensis* K. S |
| 166 | *C. cicadae* Shing | 201 | *C. cylindrica* Petch |
| 167 | Cordyceps sp. | 202 | *C. toriharamontana* K. |
| 168 | Cordyceps sp. | 203 | *C. lloydii* Faucett. |
| 169 | Cordyceps sp. | 204 | *C. elateridicola* K. S |
| 170 | *C. melolonthae* Sacc. | 205 | *C. indigotica* K. S |
| 171 | *C. paradoxa* f. sp. | 206 | *C. appendiculata* K. S |
| 172 | Isaria sp. | 207 | Podonectrioides sp. |
| 173 | Torrubiella sp. | 208 | Synnematium sp. |
| 174 | Torrubiella sp. | 209 | Cordyceps sp. |
| 175 | *T. pallida* K. S | 210 | Cordyceps sp. |
| 211 | Paecilomyces sp. | | |
| 212 | *Isaria Farinosa* f. sp. | | |
| 213 | *C. michiganensis* f. sp. | | |
| 214 | Isaria sp. | | |
| 215 | Cordyceps sp. | | |
| 216 | Hymenostilbe sp. | | |
| 217 | *C. sobolifera* f. sp. | | |
| 218 | Cordyceps sp. | | |
| 219 | Isaria sp. | | |
| 220 | *C. ferruginosa* f. sp. | | |
| 221 | Isaria sp. | | |
| 222 | *C. sinensis* (Berk.) Sacc. | | |
| 223 | *C. ishikariensis* K. S | | |
| 224 | Cordyceps sp. | | |
| 225 | Cordyceps sp. | | |
| 226 | *C. pleuricapitata* f. sp. | | |

TABLE 1

| Fruit Body layers No. | Name |
|---|---|
| CY 1 | kamemushitake |
| 2 | awafukimushitake |
| 3 | usukisanagitake |
| 4 | hachitake |
| 5 | taiwantorubierakumotake |
| 6 | usukiyokobaetake |
| 7 | sanagitake |
| 8 | kurotsubushirokumotake |
| 9 | tetsuboumushitake |
| 10 | hanayasuritake |
| 11 | hanasanagitake |
| 12 | giberuratake |
| 13 | tobidashikumotake |
| 14 | taiwanaritake |
| 15 | imomushihanayasuritake |
| 16 | tosakaimomushitake |
| 17 | kometsukimushitake |
| 18 | konasanagitake |
| 19 | edauchikamemushitake |
| 20 | kometsukishirohimetanbotake |
| 21 | osamushitake |
| 22 | tosakahanasanagitake |
| 23 | futokubikuchikimushitake |
| 24 | shiroaritake |
| 25 | mushihikiabutake |
| 26 | shirogiberuratake |
| 27 | iriomotesemitake |
| 28 | yaeyamakometsukimushitake |
| 29 | tsutsunagakumotake |
| 30 | kabuyamatsubutake |
| 31 | iriomotetsubutake |
| 32 | iriomotehanazemitake |
| 33 | togarisuzumebachitake |
| 34 | edaucshiiragaharitake |
| 35 | kanbiramushitake |
| 36 | tamasanagiharitake |
| 37 | maruminokoganemushitake |

TABLE 1-continued

| Fruit Body layers No. | Name |
|---|---|
| 38 | semitake |
| 39 | hatojimushiharitake |
| 40 | kumotake |
| 41 | tosakahanasanagitake |
| 42 | murasakikubioretate |
| 43 | dewanoimomushitake |
| 44 | mayudamatake |
| 45 | nagaenoimomushitake |
| 46 | himehanasanagitake |
| 47 | kuchikimushiharitake |
| 48 | kuchikitsutonomitake |
| 49 | tsubunosemitake |
| 50 | iragaharitake |
| 51 | himesanagitake |
| 52 | kuchikimushitsubutake |
| 53 | syakutorimushiharitake |
| 54 | edatsumarimayudamatake |
| 55 | oominosanagitake |
| 56 | mayudamaawafukimushitake |
| 57 | aritake |
| 58 | edauchiawafukimushitake |
| 59 | edauchikometsukimushitake |
| 60 | chibikonasanagitake |
| 61 | mijinkumotake |
| 62 | yokobaetake |
| 63 | sancyuusugeharitake |
| 64 | kemushikotsubuharitake |
| 65 | saodachimushitake |
| 66 | syakutorimushiawanomitake |
| 67 | chijimihanasanagitake |
| 68 | torubierakumotake |
| 69 | sancyumushitakemodoki |
| 70 | hadanitsubutake |
| 71 | sabiirokubioretake |
| 72 | edauchisabiirokubioretake |
| 73 | kumonoharisenbon |
| 74 | usukiyokobaetake |
| 75 | kaigaramushitsubutake |
| 76 | oozemitake |
| 77 | suzumegatake |
| 78 | kamabuchiooharitake |
| 79 | yanmatake |
| 80 | tsukutsukuboushisemitake |
| 81 | shirominokaigaramushitake |
| 82 | kaigaramushikonatake |
| 83 | hosoenoakakubioretake |
| 84 | usuirokuchikitsubutake |
| 85 | seminoharisenbon |
| 86 | oirasekuchikimushitake |
| 87 | unkaharitake |
| 88 | hadanibeniirotsubutake |
| 89 | tsubuawafukimushitake |
| 90 | miyamamushitake |
| 91 | towadamidorikuchikimushitake |
| 92 | gayadorikiirotsubutake |
| 93 | gayadorinagamitsubutake |
| 94 | beniimomushitake |
| 95 | kubinagakuchikimushitake |
| 96 | tsukinukihachitake |
| 97 | ariyadoritanbotake |
| 98 | usuirosemitake |
| 99 | usuirotanbotake |
| 100 | koganemushitanbotake |

TABLE 2

| Fruit Body layers No. | Name |
|---|---|
| CY 101 | oirasekemushiharitake |
| 102 | mijinimomushitake |
| 103 | fudenohosuzumegatake |
| 104 | akaminoooguramotake |
| 105 | shirooozemitake (made in Utarube) |

TABLE 2-continued

Fruit Body layers No. | Name
--- | ---
106 | michinokukoganetsubutake
107 | michinokukiirotsubutake
108 | kuchikikanotsunotake
109 | shirominokuchikimushitake
110 | kuchikiusuirotubutake
111 | umemurasemitake
112 | kengatakoganemushitake
113 | beniirokuchikimuchitake
114 | inegosemitake
115 | kusanagihimetanbotake
116 | tamasanagitake
117 | kuchikifusanomitake
118 | kotsubusanagiharitake
119 | ameirotsubutake
120 | kuchikimushikoganetsubutake
121 | kotsubuimomushiharitake
122 | osamushitanbotake
123 | edauchitanbotake
124 | ezotanbotake
125 | ezohanayasuritake
126 | eriashitanbotake
127 | tanbotakemodoki
128 | hanayasuritake
129 | himetanbotake
130 | numeritanbotake
131 | minazukitanbotake
132 | miyamatanbotake
133 | giberuratsubutake
134 | kumonomomogatsubutake
135 | kumonokouratsubutake
136 | sangokumotake
137 | kumonoootogaritsubutake
138 | kumonoetsukitsubutake
139 | koedakumotake
140 | hasunomikumotake
141 | tsukidashihasunomikumotake
142 | mikanirokumotake
143 | usujirokumotake
144 | tsukidashinagaminokumotake
145 | kogomekumotake
146 | momoirokumotake
147 | nadagirionigumotake
148 | sakibutokaigaramushitake
149 | harigatakaigaramushitake
150 | kaigaramushikiirotsubutake
151 | futokubihaeyadoritake
152 | ezoharuzemitake
153 | eniwasemitake
154 | tobishimasemitake
155 | aburazemitake
156 | ariyadoritanbotake
157 | konaabutake
158 | mayasanetsukimushitake
159 | koganekumotake
160 | iriomotetorubierakumotake
161 | okunitsukawakumotake
162 | mijinshirokumotake
163 | amamihanazemitake
164 | usuirokogomisemitake
165 | ainusemitake
166 | kiashioozemitake
167 | itohikimijinaritake
168 | ishikarihanayasuritake
169 | himeyadoribaetake
170 | takedakometsukimushitake
171 | usuirowamemurasemitake
172 | hanaimomushitake
173 | hagakureshirotsubutake
174 | nagaminokumotake
175 | usukiooanikumotake
176 | kobugataaritake
177 | usuakasyakutorimushitake
178 | shirohimesanagitake
179 | usukitanbosemitake
180 | ashigurokuoretake
181 | kubiorearitake
182 | usuirohimefutobaritake
183 | nagatsubuharitake
184 | kanzashisemitake
185 | oguramushitake
186 | himekubioretake
187 | himeharitake
188 | himeharuzemitake
189 | himehadakasemitake
190 | marumikuroharitake
191 | jiimusyadoritake
192 | kurominokuchikimushitake
193 | koganeimomushitake
194 | hanekakusyakudoritake
195 | koganemushihanayasuritake
196 | kusagimushitake
197 | abuyadoritake
198 | minomushishirosanagitake
199 | haeyadoritogaritsubutake
200 | ogurakomotake

TABLE 3

Fruit Body layers No. | Name
--- | ---
CY 201 | iriomotekumotake
202 | tanboezozemitake
203 | kuchikigasunomiaritake
204 | yaeyamakometsukimushitake
205 | midoritosakatake
206 | edauchitsutonomitake
207 | yokobaenoshiroigatake
208 | hanaaburazemitake
209 | kubiorekaigaramushitake
210 | usukigomimushitake
211 | kamemushinomayudamatake
212 | konausukisanagitake (Isaria-type)
213 | garasukuchikitsubutake
214 | hanaabutake
215 | hainohimeharitake
216 | syuiroyanmatake
217 | shirosemitake
218 | chabotanbotake
219 | kabutomushikonaharitake
220 | akaenokubioretake
221 | iriomotekonazemitake
222 | fuyumushinatsukusa-korujisetsubusushinenshisu
223 | minomushishirosanagitake
224 | abukumatanbotake
225 | mijinhimesanagitake
226 | kiashitanbotake Polypore organisms that may be employed in the present invention are as follows.

(1) Kofukisarunokoshikake-fungus (*Elfvingia applanata*), (2) Kikobutake-fungus, (3) Kujiratake-fungus, (4) Ego-nokitake-fungus (*Dadaleopsis styracina*), (5) Chakaigaratake-fungus (*Dadaleopsis tricolor*), (6) Tsuriganetake-fungus (*Fomes fomentarius*), (7) Ezohizumetake-fungus, (8) Kawaratake-fungus (*Coriolus-versicolor*), (9) Aragekawaratake-fungus (*Coriolus hirsutus*), (10) Niresarunokoshikake-fungus, (11) Shutake (*Pycnoporus cinnabarinus*), (12) Mannentake-fungus (*Ganoderma lucidum*), (13) Maitakefungus (*Grifola frondosa*), and (14) Yanitake-fungus Other fimgi that may be employed in the present invention are (1) Shiitake-fungus (*Lentinus edodes*), (2) Donkoshiitake-fungus and (3) Matsutake-fungus (*Tricholoma matasutake*) and the like.

The immune-enhancing food according to the invention may be a metabolite fluid containing a fruit body (sexual generation and nonsexual generation), and a mycelium of Isaria-type insect-raised fungus (*Cordyceps japonensis*) as an active ingredient, and may also be a mixture thereof with Ogi-fungus extract, beta-carotene and polypore extract. The immune-enhancing food may be a fluid, a semi-solid or a solid. The immune-enhancing food according to the present invention may be a paste, jam, jelly and the like when provided as a semi-solid, or it may be a powder, particle, granule and tablet when provided as a solid.

The immune-enhancing food according to the present invention may be obtained by lyophilizing the wet fruit body (sexual generation and nonsexual generation), the mycelium and the metabolite fluid or the admixture of the fruit body (sexual generation and nonsexual generation), the mycelium and the metabolite fluid with an Ogi-fungus extract, beta-carotene and polypore extract. The lyophilized material may then be pulverized followed by admixing with appropriate binders (e.g., honey, syrup, gum arabic, gelatin, sorbitol, tragacanth, polyvinyl pyrrolidone and the like), excipients (e.g., lactose, sugar, starches from cereals such as unpolished rice, pearl barley and corn, calcium phosphate, sorbitol, glycine and the like), disintegrants (potato starch and the like), or coatings (gelatin, white sugar, hydropropyl cellulose and the like) to formulate the food into a product in the form of a powder, particle, granule, tablet, jelly, liquid, capsule and the like. The pulverizing may preferably be conducted so that a particle size from about 20 to about 400 microns is obtained, while the granulating may preferably be conducted so that a particle size from about 0.5 to 3 mm is obtained.

Alternatively, the immune-enhancing food comprising the fruit body (sexual generation and nonsexual generation), the mycelium and the metabolite fluid of Isaria-type insect-raised fungus (*Cordyceps Japonensis*) as a main ingredient, according to the invention or the admixture thereof with Ogi-fungus extract, beta-carotene and polypore extract, may be admixed with the ingredients of confectioneries to be served cooled, at ambient temperature, or warmed, or the food may be converted into a cream to be incorporated into confectioneries, health-oriented foods, convenience foods, noodles (dry noodles and raw noodles), soups, delicatessen foods and the like.

The present invention is further described in the following examples, which are not intended to restrict the present invention in any way.

EXAMPLE 1

METHOD OF PREPARING STARTING MATERIAL (a) Method of Preparing a Fruit Body (Sexual Generation and Nonsexual Generation, a Mycelium and a Metabolite Fluid of Hanasanagitake-Fungus (*Isaria Japonica* Lloyd), An Isaria-Type Insect-Raised Fungus (*Cordyceps Japonensis*)

Stock cells of *Isaria japonica* Lloyd were inoculated into a medium consisting of 0.1% to 2.0% of glucose, 0.1% to 2.0% of dried yeast (Iwaki), 0.01% to 0.1% of inosine and 1.0% of agar, and subjected to separation incubation on an agar slant in a tube. After incubation at 10° C. to 30° C. for 14 to 21 days, the resulting fruit bodies were similar morphologically and microscopically to those occurring naturally. These resulting fruit bodies were used as a source inoculant for artificial incubation.

Bulk culture fluid medium was obtained by inoculating the source inoculant aseptically into a liquid medium containing 0.1% to 2.0% of glucose and 0.1% to 2.0% of dried yeast, followed by incubation at 10° C. to 30° C., preferably at 18° C., for 21 to 35 days. In this fluid medium, aggregated mycelium was formed. The metabolite fluid had no taste or odor, and was slightly turbid or slightly pale yellow, but gradually became transparent. The fruit body (sexual generation and nonsexual generation), the mycelium and the netabolite fluid, after lyophilization, had the composition shown in Table 2.

TABLE 2

| Ingredient | Concentration |
| --- | --- |
| Water | 9.9 (g/100 g) |
| Crude proteins | 7.1 (g/100 g) |
| Crude fats | 5.0 (g/100 g) |
| Carbohydrates | 76.3 (g/100 g) |
| Minerals | 1.7 (g/100 g) |

The amino acid composition of the proteins contained in the lyophilized product is shown in Table 3.

TABLE 3

| Amino acid | Concentration µg/mg) |
| --- | --- |
| Aspartic acid | 6.136 |
| Threonine | 2.573 |
| Serine | 3.163 |
| Glutamic acid | 10.608 |
| Prorine | 3.005 |
| Glycine | 3.311 |
| Alanine | 4.045 |
| Cystine | 0.817 |
| Valine | 3.854 |
| Methionine | 1.373 |
| Isoleucine | 2.702 |
| Leucine | 5.496 |
| Tyrosine | 2.645 |
| Phenylalanine | 3.502 |
| Histidine | 1.629 |
| Lysine | 2.500 |
| Arginine | 4.965 |

(b) i. Method of Preparation of Ogi-Fungus Extract 15 g of pulverized dried root of Ogi-fungus was added to 100 g of water, and the mixture was boiled at a temperature from 70° C. to 100° C. for 6 hours. The mixture was allowed to stand until the production of insoluble substances was completed, then the insoluble materials were separated off to yield about 1 g of Ogi-fungus extract.

ii. Beta-Carotene

Commercially available carotene base-30 (Takada Koryo) was employed.

iii. Method of Preparation of Polypore Extract 18 g of dried pulverized root of Polypore was added to 100 g of water, and the mixture was boiled at a temperature of 95° C. for 6 hours. The mixture was allowed to stand until the production of insoluble substances was completed, then the insoluble materials were separated off to yield about 6 g of Polypore extract.

EXAMPLE 2

METHOD OF PRODUCING IMMUNE-ENHANCING FOOD AS LIQUID MATERIAL (a) An Example Wherein the Fruit Body (Sexual Generation And Nonsexual Generation), The Mycelium and the Metabolite Fluid of *Isaria Japonica* Lloyd Was Employed as a Main Ingredient 2.5 parts by weight of the fruit body (sexual and nonsexual generations), 2.5 parts by weight of the mycelium and 95 parts by weight of the metabolite fluid of *Isaria japonica* Lloyd obtained in Example 1(a) were stirred thoroughly, and the fruit body (sexual generation and nonsexual generation) and the mycelium were dissolved in the metabolite fluid. After sterilization at a high temperature of 105° C. for 1 hour, the inventive immune-enhancing food, which was a transparent fluid, was poured into a bottle.

(b) An Example Wherein the Fruit Body (Sexual Generation And Nonsexual Generation), The Mycelium and the Metabolite Fluid of *Isaria Japonica* Lloyd Was Admixed With Ogi-Fungus Extract, Beta-carotene And Polypore Extract 2.5 parts by weight of the fruit body (sexual generation and nonsexual generation), 2.5 parts by weight of the mycelium and 95 parts by weight of the metabolite fluid of *Isaria japonica* Lloyd obtained in Example 1(a) were stirred thoroughly and admixed with 1 part of the Ogi-fungus extract, 0.1 part of the beta-carotene and 1 part of the Polypore extract obtained in steps, i, ii and iii in Example 1(b). After sterilization at a high temperature of 105° C. for 1 hour, the inventive immune-enhancing food, which was a transparent fluid, and poured into a bottle.

EXAMPLE 3

METHOD OF PRODUCING IMMUNE-ENHANCING FOOD AS SOLID MATERIAL (a) An Example Wherein the Fruit Body (Sexual Generation and Nonsexual Generation), the Mycelium and the Metabolite Fluid of *Isaria Japonica* Lloyd Were Employed as a Main Ingredient 2.5 parts by weight of the fruit body (sexual generation and nonsexual generation), 2.5 parts by weight of the mycelium and 95 parts by weight of hte metabolite fluid of *Isaria japonica* Lloyd obtained in Example 1(a) were lyophilized and pulverized. 2 parts of the powder thus obtained was admixed with 98 parts of lactose, and the mixture was granulated or solidified.

(b) An Example Wherein the Fruit Body (Sexual Generation And Nonsexual Generation), The Mycelium and the Metabolite Fluid of *Isaria Japonica* Lloyd Were Admixed with Ogi-Fungus Extract, Beta-Carotene and Polypore Extract 2.5 parts by weight of the fruit body (sexual generation and nonsexual generation), 2.5 parts by weight of the mycelium and 95 parts by weight of the metabolite fluid of *Isaria japonica* Lloyd obtained in Example 1(a) were stirred thoroughly and admixed with 1 part of Ogi-fungus extract, 0.1 part of beta-carotene and 1 part of Polypore extract obtained in steps i, ii and iii in Example 1(b). After lyophilization, 2 parts of the powder thus obtained was admixed with 98 parts of lactose, and the mixture was granulated or solidified.

EXAMPLE 4

METHOD OF PRODUCING IMMUNE-ENHANCING FOOD AS SEMI-SOLID MATERIAL (a) An Example Wherein the Fruit Body (Sexual Generation and Nonsexual Generation), the Mycelium and the Metabolite Fluid of *Isaria Japonica* Lloyd Were Employed as Main Ingredients To 10 parts of the powder obtained by lyophilization of the fruit body (sexual generation and nonsexual generation), mycelium and metabolite fluid of *Isaria japonica* Lloyd obtained in Example 1(a), 80 parts of honey, 10 parts of water and 0.05 part of sodium benzoate or benzoic acid were added and mixed thoroughly to obtain a semi-solid immune-enhancing food.

(b) An Example Wherein the Fruit Body (Sexual Generation and Nonsexual Generation), the Mycelium and the Metabolite Fluid of *Isaria Japonica* Lloyd Were Admixed with Ogi-Fungus Extract, Beta-Carotene and Polypore Extract To 100 parts of the metabolite fluid containing the fruit body (sexual generation and nonsexual generation) and the 2mycelium of *Isaria japonica* Lloyd obtained in Example 3(b), 1 part of Ogi-fungus extract, 0.1 part of beta-carotene and 1 part of Polypore extract were admixed and lyophilized. To 10 parts of the powder thus obtained, 80 parts of honey, 10 parts of water and 0.05 part of sodium benzoate or benzoic acid were added and mixed thoroughly to obtain a semi-solid, immune-enhancing food.

Experiments

Immune-activating effects of the inventive immune-enhancing foods were evaluated as follows.

Experiment 1

(1) Materials (a) Experimental animals: $CDF_1$ mice were purchased from Nippon SLC Co. The animals were acclimatized in an animal room at a temperature of 23° C.±1° C. and a humidity of 50% ±5% for 1 week or longer after purchase, and 4 to 8 $CDF_1$ mice of the age from 6 to 8 weeks were assigned to one group.

(b) Culture medium and immunological reagents: 10.4 g of RPHI 1640 (Nissui Seiyaku Co.) and 2.3 g of HEPES (N-2-hydroxyethyl-piperazine-N'-ethanesulfonic acid, Dojin Iyaku Kako Co.) were dissolved in 900 ml of deionized water, and the solution was subjected to high pressure steam sterilization. Separately, 0.29 g of L-glutamic acid, 0.11 g of sodium pyruvate, 2.0 g of sodium hydrogen carbonate (all three from Wako Jun-yaku Co.), and 0.06 g of kanamycin sulfate (Heiji Seika Co.) were dissolved in 100 ml of deionized water, and the solution was sterilized by filtration through a 0.22 micrometer membrane filter (Millipore Co.), and the filtrate was added to 900 ml of the culture medium obtained above to make a final volume of 1000 ml. The culture was conducted in the presence of 2-ME (2-mercaptoethanol) at a final concentration of $5 \times 10^{-5}$M as well as Fetal Bovine Serum (FBS). FBS was obtained from General Scientific Laboratory Co. as a mycoplasma free product, and was inactivated at 56° C. for 30 minutes prior to use.

To prepare a suspension of ovine red blood cells (SRBC), SRBC were separated from ovine blood from Nippon Biotest Co. and washed twice by centrifugation while cooling (2,000 rpm, 10 minutes) to obtain packed cells. The cells thus obtained were resuspended into culture medium at suitable concentrations.

To prepare a guinea pig serum, male Hartley guinea pigs purchased from Nippon SLC Co. were acclimatized under typical condition, and then blood was taken from the hearts of the guinea pigs and then filled in a polypropylene tube (Falcon Co.), which was allowed to stand at room temperature for 1 hour. After clotting, the blood was centrifuged (3,000 rpm, 20 minutes) and then further centrifuged (2,000 rpm, 10 minutes) to remove the contaminating red blood cells. The recovered supernatant was mixed with SRBC and mouse spleen cells, then centrifuged (10,000 rpm, 30 minutes) while subjected to cooling, and then stored at −80° C. in a freezer until use.

Other reagents used were biochemical grade products from Wako Jun-yaku Co.

(2) Counting of antibody producing cells (PFC) against SRBC

Cunningham's method modified by Hasimoto et al.[4] was employed. A predetermined amount of the immune-enhancing food obtained in Example 3(b) was weighed and administered as a solution in physiological saline.

[4] Y. Hasimoto, T. Sudo, F. Hamaoka, Igaku no Ayumi, 62, 824 (1967)

The immune-enhancing food was administered orally to CDF male mice once a day for a period of 6 days starting on the 4th day before the day of challenge (including the day of challenge). On the 4th day of the period (i.e., the day of challenge), 0.2 ml of 10% (v/v) SRBC suspension ($2 \times 10^8$ cells) was injected via tail vein to effect immunization. After 4 days, the mice were exsanguinated, and the spleens were extracted and ground in a serum-free culture medium to obtain a spleen cell suspension. After centrifugation three times while cooling (1,500 rpm, 5 minutes), the cells were resuspended at $4 \times 10^7$ cells/ml in 1% FBS-supplemented medium to obtain an antibody-producing cell source. 0.1 ml of this spleen cell suspension, 0.5 ml of 10% (v/v) SRBC suspension formulated in 1% FBS-supplemented culture medium, and 0.4 ml of 4-fold-diluted guinea pig serum were placed in a tube and mixed thoroughly. The mixture was infused into a paraffin film slide chamber and the both ends of the groove were closed with paraffin. After allowing the mixture to stand for 1 hour at 37° C. in 5% $CO_2$ flow, the hemolytic plaques were counted microscopically ($4 \times 10$ magnification). PFC count per $10^6$ spleen cells was calculated according to the formula shown below.

$$N = n/(A \times B)$$

wherein n: represents the mean of PFC count in 3 slide chambers,

A: represents the number of spleen cells in 1 ml of cell (N) fluid, and

B: represents the volume of the chamber (ml).

The values obtained are represented as mean standard deviation, and the significant difference between the groups was analyzed by the Student t test.

(3) Immune-activating effect of the inventive immune-enhancing food 3, 10 and 30 mg/kg of the inventive immune-enhancing food obtained in Example 3(b) were administered once a day for a period of 6 days, during which period the antigen was administered. The immune-activating effects observed in the treatment groups are shown in FIG. 1, wherein the doses of the immune-enhancing food containing insect-raised fungus metabolite fluid, etc., as a main ingredient vs antibody-producing cell count/$10^2 \times$spleen cells (i.e., number of immune cells) are represented as abscissa vs ordinate.

Figure 1:
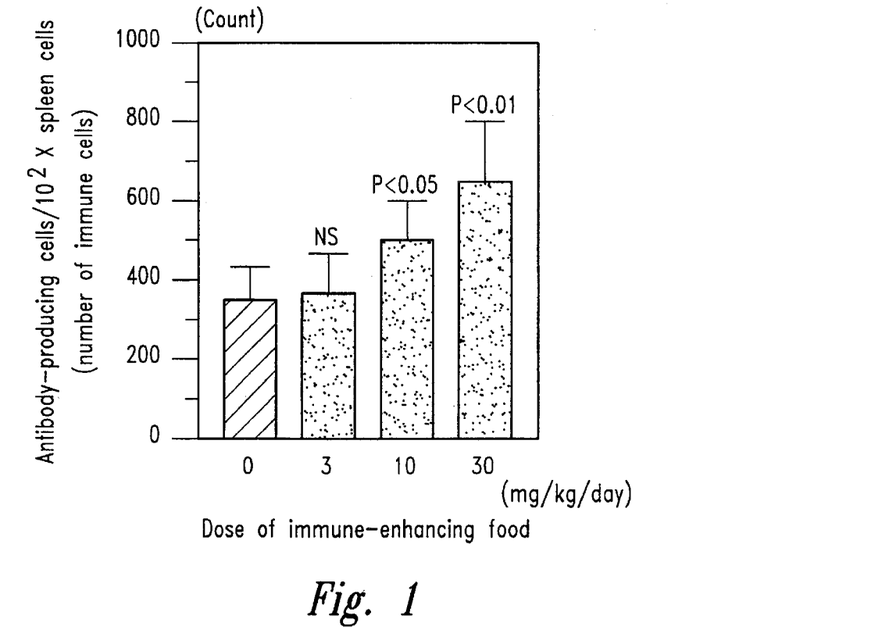
FIG. 1 depicts a graph indicating antibody-producing cell count/$10^2$×spleen cells (i.e., the number of immune cells) when the inventive immune-enhancing food, which contains insect-raised fungus metabolite fluid, etc., as a main ingredient, was given once a day for 6 days in total before and after the day of antigen sensitization.

In FIG. 1, NS denotes "no significant difference," and P represents statistical "reliability and probability." For example, P<0.01 means that a reliable result is obtained in 99 out of 100 times. The height of the graph represents the mean, while the bar attached to the top of the graph represents the variation of the data, which is called the standard deviation.

As shown in FIG. 1, the inventive immune-enhancing food containing the fruit body (sexual generation and non-sexual generation), the mycelium and the metabolite fluid of Isaria-type insect-raised fungus (Cordyceps Japonensis), together with Ogi-fungus extract, beta-carotene and *Elfvingia applanata* extract, had a statistically significant immune-activating effect in any of the groups treated at 10 mg/kg/day and 30 mg/kg/day.

Experiment 2

In order to control the expression of the effects of an immune system activator, the timing of the administration of the activator in relation to administration of the antigen is generally considered to be important.

An inventive immune-enhancing food similar to that used in Experiment 1 was administered at 3, 10 and 30 mg/kg once a day for 3 days before SRBC antigen administration day (inclusive). In a manner similar to Experiment 1, the spleens were extracted from the animals, and the effects on immune functioning were examined. Antibody-producing cells/$10^2 \times$spleen cells (number of immune cells) when the inventive food was administered once a day for 3 days before the antigen sensitization (inclusive), are shown in FIG. 2.

Figure 2:
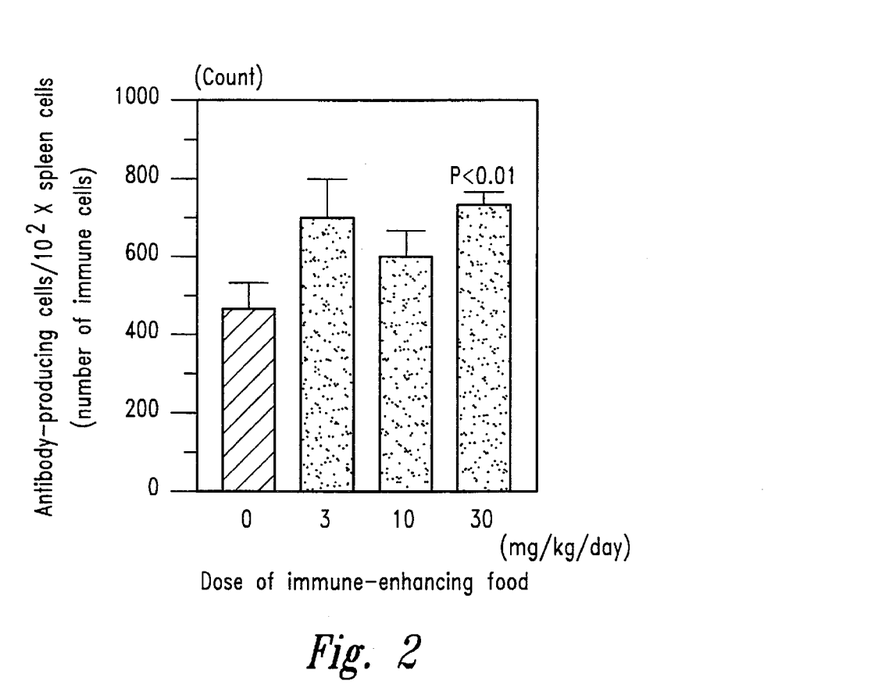
FIG. 2 depicts a graph indicating antibody-producing cell count/$10^2$×spleen cells (i.e., number of immune cells) when the inventive immune-enhancing food, which contains insect-raised fungus metabolite fluid, etc., as a main ingredient, was given once a day for 3 days before the day of antigen sensitization, including the day of antigen sensitization.

As is evident from FIG. 2, the inventive immune-enhancing food had statistically significant immune-activating effects when dosed once a day at 30 mg/kg for 3 days including the day of antigen sensitization.

Figure 3:
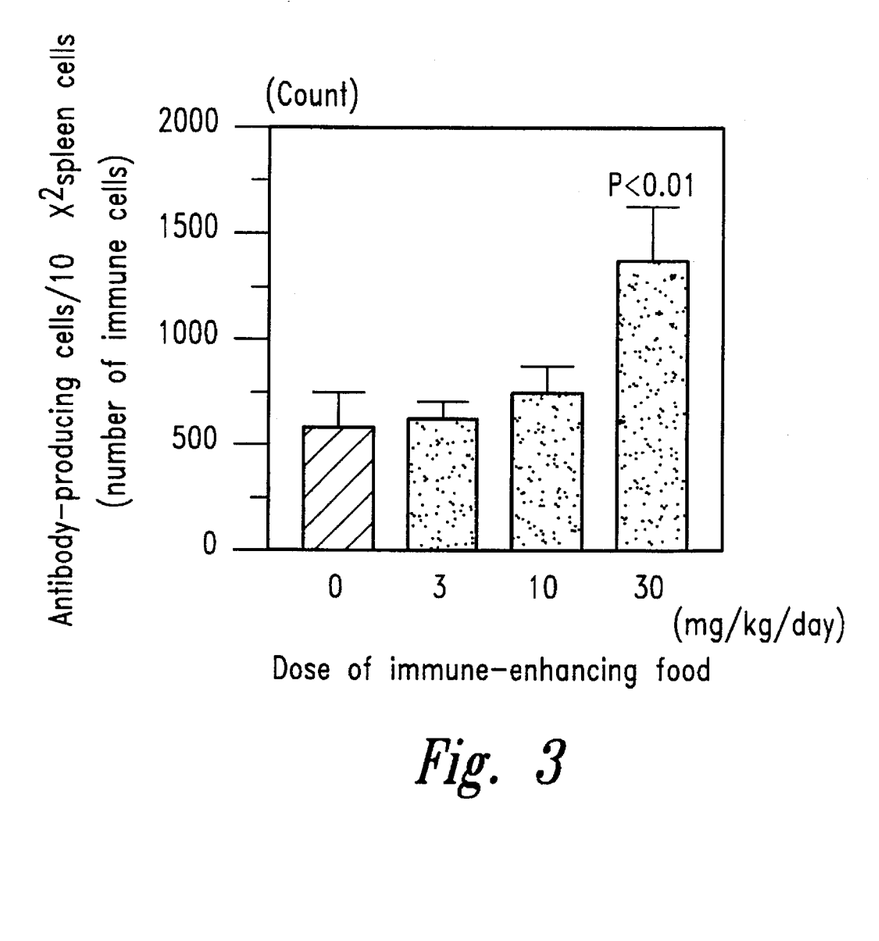
FIG. 3 depicts a graph indicating antibody-producing cell count/$10^2$×spleen cells (i.e., number of immune cells) when the inventive immune-enhancing food, which contains insect-raised fungus metabolite fluid, etc., as a main ingredient, was given once a day for 3 days after the day of antigen sensitization, including the day of the antigen sensitization.

An inventive immune-enhancing food similar to that used in Experiment 1 was post-administered at 3, 10 and 30 mg/kg once a day for 3 days including the day of SRBC antigen administration, and the results shown in FIG. 3 were obtained.

As is evident from FIG. 3, the inventive immune-enhancing food had statistically significant immune-activating effects when post-dosed once a day at 30 mg/kg for 3 days including the day of antigen administration. The results in Experiment 2 indicate that the inventive immune-enhancing food exhibits immune-activating effects when given not only before the antigen sensitization but also after the antigen sensitization.

When Konasanagitake-fungus, which is also one of the organisms of Isaria-type insect-raised fungi (*Cordyceps japonenis*), was subjected to experiments similar to those described above, similar results were obtained.

Advantage of the invention

Conventional immune-enhancing substances exhibit immune-activating effects only when administered intraperitoneally and intravenously, resulting in difficulty in handling. On the contrary, the inventive immune-enhancing food can be ingested readily as a food because of its ability to display immune enhancing effects even when administered orally, and thus can be used in self-controlled therapy to prevent and/or treat various infections and tumors because of the ability of the food to exhibit excellent immune-activating effects regardless of the timing of the administration in relation to the antigen sensitization.

What is claimed is:

1. An immune-enhancing food comprising a fruit body, mycelium and metabolite fluid of Isaria-type insect-raised fungus (*Cordyceps japonensis*) as a main ingredient.

2. An immune-enhancing food comprising an Ogi (*Gomphidius roseus*) extract, a beta-carotene and a polypore extract admixed with the fruit body, mycelium and metabolite fluid of Isaria-type insect-raised fungus (*Cordyceps japonensis*) according to claim 1.

3. An immune-enhancing food according to claim 2, obtained by admixing 0.1 to 2 parts by weight of said Ogi (*Gomphidius roseus*) extract, 0.1 to 1 part by weight of said beta-carotene and 1 to 10 parts by weight of said polypore extract with 100 parts by weight of said with fruit body, mycelium and metabolite fluid of Isaria-type insect-raised fungus (*Cordyceps japonensis*).

4. An immune-enhancing food according to claim 1, 2, or 3 wherein said Isaria-type insect-raised fungus (*Cordyceps japonensis*) is Hanasanagitake-fungus (*Isaria japonica* Lloyd) or Konasanagitake-fungus.

5. An immune-enhancing food according to claim 1 wherein said food comprising said fruit body, mycelium and metabolite fluid of Isaria-type insect-raised fungus (*Cordyceps japonensis*) is a liquid.

6. An immune-enhancing food according to claim 1 wherein said food comprising said fruit body, mycelium and metabolite fluid of Isaria-type insect-raised fungus (*Cordyceps japonensis*) is a semi-solid.

7. An immune-enhancing food according to claim 1 wherein said food comprising said fruit body, mycelium and metabolite fluid of Isaria-type insect-raised fungus (*Cordyceps japonensis*) is a solid.

* * * * *